United States Patent
Catheline et al.

(10) Patent No.: US 10,485,516 B2
(45) Date of Patent: Nov. 26, 2019

(54) SHEAR WAVE GENERATION METHOD, SHEAR WAVE IMAGING METHOD AND THERMAL MAPPING OR TREATING METHOD UTILIZING SUCH A GENERATION METHOD AND INSTALLATION FOR GENERATING AT LEAST ONE SHEAR WAVE

(71) Applicants: INSTITUT NATIONAL DE LA SANTE ET DE LA RECHERCHE MEDICALE (INSERM), Paris (FR); UNIVERSITE CLAUDE BERNARD LYON 1, Villeurbanne (FR)

(72) Inventors: Stefan Catheline, Lyons (FR); Remi Souchon, Lyons (FR); Ali Zorgani, Lyons (FR); Jean-Yves Chapelon, Lyons (FR)

(73) Assignees: INSTITUT NATIONAL DE LA SANTE ET DE LA RECHERCHE MEDICALE (INSERM), Paris (FR); Université Claude Bernard Lyon 1, Villeurbanne (FR); Centre Léon-Bérard, Lyons (FR)

(*) Notice: Subject to any disclaimer, the term of this patent is extended or adjusted under 35 U.S.C. 154(b) by 478 days.

(21) Appl. No.: 15/119,458
(22) PCT Filed: Feb. 26, 2015
(86) PCT No.: PCT/EP2015/054002
§ 371 (c)(1),
(2) Date: Aug. 17, 2016
(87) PCT Pub. No.: WO2015/128409
PCT Pub. Date: Sep. 3, 2015

(65) Prior Publication Data
US 2017/0007206 A1    Jan. 12, 2017

(30) Foreign Application Priority Data
Feb. 26, 2014 (EP) .................................. 14305267

(51) Int. Cl.
*A61B 8/00* (2006.01)
*A61B 5/055* (2006.01)
(Continued)

(52) U.S. Cl.
CPC ............ *A61B 8/485* (2013.01); *A61B 5/0066* (2013.01); *A61B 5/015* (2013.01); *A61B 5/055* (2013.01);
(Continued)

(58) Field of Classification Search
CPC ..... A61B 8/485; A61B 8/4488; A61B 8/4466; A61B 5/015; A61B 5/0066; A61B 8/4477;
(Continued)

(56) References Cited

U.S. PATENT DOCUMENTS 5,428,999 A   7/1995 Fink
8,647,276 B2  2/2014 Tabaru et al.
(Continued)

FOREIGN PATENT DOCUMENTS

JP   H06-341978    12/1994
WO   2011-027644   3/2011

OTHER PUBLICATIONS

B. E. Anderson, R. A. Guyer, T. J. Ulrich, and P. A. Johnson, "Time reversal of continuous-wave, steady-state signals in elastic media," Appl. Phys. Lett., 94, 11198 (2009).*
(Continued)

*Primary Examiner* — Bill Thomson
*Assistant Examiner* — Aminah Asghar
(74) *Attorney, Agent, or Firm* — Young & Thompson (57) ABSTRACT

Method for generating a shear wave in a target region of a soft solid, includes the following steps: a) generating at least
(Continued)

two shear waves with a first and a second source of shear waves in the target region; b) detecting a propagation pattern of the shear wave in the target region with a detector unit including a row of ultrasonic transducers aligned on a first direction perpendicular to a detection direction of each or a single ultrasonic transducer movable along a first direction perpendicular to its detection direction; c) proceeding to a time reversal of the detected propagation pattern; and d) submitting the target region to an inverted excitation set of forces based on the temporally inverted propagation pattern. During step b), a first propagation pattern is detected when only the first source is active and a second propagation pattern is detected when only the second source is active.

21 Claims, 5 Drawing Sheets

(51) Int. Cl.
  *A61B 8/08* (2006.01)
  *G01S 15/89* (2006.01)
  *G01S 7/52* (2006.01)
  *A61B 5/00* (2006.01)
  *A61B 5/01* (2006.01)

(52) U.S. Cl.
  CPC .......... *A61B 8/4416* (2013.01); *A61B 8/4466* (2013.01); *A61B 8/4477* (2013.01); *A61B 8/4488* (2013.01); *G01S 7/52022* (2013.01); *G01S 15/8918* (2013.01); *G01S 15/8977* (2013.01)

(58) Field of Classification Search
  CPC .............. G01S 15/8977; G01S 15/8918; G01S 7/52022
  See application file for complete search history.

(56) References Cited

U.S. PATENT DOCUMENTS

2007/0274156 A1* 11/2007 Fink ........................ G10K 11/02
                                                                                   367/87
2011/0066030 A1    3/2011 Yao
2014/0160882 A1*  6/2014 Vu ........................ G01V 1/006
                                                                                   367/7
2014/0330122 A1* 11/2014 Baghani ................ A61B 8/485
                                                                                   600/438

OTHER PUBLICATIONS

B.E. Anderson, R.A. Guyer, T. J. Ulrich, and P.A. Johnson, "Time reversal of continuous-wave, steady-state signals in elastic media," Appl. Phys. Lett., 94, 11198 (2009). (Year: 2009).*

Benech et al., "Elasticity Estimation by Time-Reversal of Shear Waves," 2007 IEEE Ultrasonics Symposium Proceedings, New York City, NY, USA, Oct. 28-31, 2007, vol. 5 of 6, pp. 2263-2266.

Benech et al., "1-D Elasticity Assessment in Soft Solids from Shear Wave Correlation: The Time-Reversal Approach," IEEE Transactions on Ultrasonics, Ferroelectrics and Frequency Control, vol. 56, No. 11, Nov. 2009.

S. Catheline et al.: "Time Reversal of Elastic Waves in Soft Solids", Physical Review Letters, vol. 100, No. 6, Feb. 1, 2008 (Feb. 1, 2008), XP055149130, ISSN: 0031-9007, DOI: 10.1103/PhysRevLett. 100.064301.

Benech N et al.: "Monitoring local temperature changes in soft tissues by time-reversal elastography", Ultrasonics Symposium (IUS), 2009 IEEE International, IEEE, Piscataway, NJ, USA, Sep. 20, 2009 (Sep. 20, 2009), pp. 2414-2417, XP031654469, ISBN: 978-1-4244-4389-5.

S. Catheline et al.: "Tomography from diffuse waves: Passive shear wave imaging using low frame rate scanners", Applied Physics Letters, vol. 103, No. 1, Jan. 1, 2013 (Jan. 1, 2013), pp. 014101, XP055149176, ISSN: 0003-6951, DOI: 10.1063/1.4812515.

J-L Thomas et al: "Ultrasonic beam focusing through tissue inhomogeneities with a time reversal mirror: application to transskull therapy", IEEE Transactions on Ultrasonics, Ferroelectrics and Frequency Control, IEEE, US, vol. 43, No. 6, Nov. 1, 1996 (Nov. 1, 1996), pp. 1122-1129, XP011437475, ISSN: 0885-3010, DOI: 10.1109/58.542055.

International Search Report, dated Jun. 3, 2015, from corresponding PCT application.

FR Search Report, dated Oct. 28, 2014, from corresponding FR application.

* cited by examiner

SHEAR WAVE GENERATION METHOD, SHEAR WAVE IMAGING METHOD AND THERMAL MAPPING OR TREATING METHOD UTILIZING SUCH A GENERATION METHOD AND INSTALLATION FOR GENERATING AT LEAST ONE SHEAR WAVE

TECHNICAL FIELD OF THE INVENTION

This invention relates to a method for generating at least one shear wave in a target region of a soft solid. This invention also relates to a shear wave imaging method and to a thermal mapping method for collecting information on a target region of a soft solid. This invention also concerns a method for thermally treating a target region of a soft solid. This invention also relates to an installation for generating at least one shear wave in a target region of a soft solid, this installation being useful to implement the above-mentioned methods.

In the meaning of the present invention, a soft solid is an organic tissue which can have an animal or vegetal origin. For instance, such a soft solid can be an organ of a human body, of an animal body or of a vegetable. A soft solid can also be an aliment, e.g. cheese, or a non metallic part of prosthesis, made of a natural or synthetic material.

BACKGROUND OF THE INVENTION

Shear wave elastography has been known for several years as an efficient technique for detecting an inhomogeneity of elasticity in a soft solid, such as a tumour. This technique is based on the detection of shear waves propagation speeds. Such a detection can be based on ultrasonic technology or on a magnetic resonance imaging (MRI) technology.

Shear waves can also be used to increase locally the temperature of a soft solid. This can be used as a basis for a thermal mapping method or for a method for thermally treating a target region of a soft solid, including non therapeutical aspects in the case of a non living soft solid, such as cheese or a part of a prosthesis.

In a soft solid, shear waves propagate at a speed in the range of 1 to several meters per second (m/s) and this speed can be used to characterize a target region of a soft solid, since the speed pattern of these waves allows generating images representative of the shear elastic modulus of this target region. This shear elastic modulus approximatively corresponds to the elasticity which can be sent by palpation and is ranging from a few hundreds Pa to a few thousands kPa.

In the field of therapeutical physics, an article published in Physical Review Letters (PRL 100, 064 301 (2008)) entitled «Time reversal of elastic waves in soft solids» by Catheline et al. teaches that a shear wave generated by a single generator and propagating within an agar-gelatin phantom can undergo a time reversal. Agar-gelatin can be used from a theoretical point of view, but such a material is not representative of soft solids that could be used for practical and industrial applications. This derives from the damping feature of the real soft solids with respect to shear waves. This damping feature makes this known method relatively inaccurate.

Moreover, this known method is based on a linear behaviour of the agar-gelatin phantom which constitutes the medium through which the shear waves propagate. In some cases, it might be necessary to obtain a non-linear behaviour of the medium, which cannot be obtained with the known methods because the induced stress level is not high enough for this. Actually, because of their intrinsic technology, none of the commercial elastography methods is able to deliver a shear wave amplitude in the non linear regime.

In fact, the linear behaviour of a medium is a simplistic approximation of the actual behaviour of a soft solid which might not be sufficient to distinguish two different portions of a target zone. For instance, a benign tumour and a malignant tumour might have the same elastic behaviour, which does not allow a differentiation of these tumours with a shear wave imaging method based on an elastic behaviour of the soft solid. On the other hand, a benign tumour and a malignant tumour might have different non-linear behaviours, which allows differentiating them under some circumstances.

Similar limitations occur when one needs to significantly increase the temperature of a target region of soft solid. If the stress level obtained with the shear waves is not high enough, the temperature increase of the medium is not significant.

SUMMARY OF THE INVENTION

This invention aims at solving the problems of the known techniques with a new method which is efficient to generate shear waves with a stress level high enough to obtain a non-linear behaviour of the soft solid or to significantly increase its temperature.

To this end, the invention concerns a method for generating at least one shear wave in a target region of a soft solid, this method including at least the following steps:
  a) generating at least one shear wave in the target region;
  b) detecting a propagation pattern of the least one shear wave in the target region;
  c) proceeding to a time reversal of the detected propagation pattern;
  d) submitting the target region to an excitation set of forces based on the temporally inverted propagation pattern. This method is characterized in that:
  step a) is implemented by generating at least two shear waves with at least a first source of shear waves and at least a second source of shear waves;
  step b) is implemented with a detector unit which includes:
    a row of ultrasonic transducers aligned on a first direction perpendicular to a detection direction of each ultrasonic transducer or
    a single ultrasonic transducer movable along a first direction perpendicular to its detection direction
  during step b), a first propagation pattern is detected when only the first source is active and a second propagation pattern is detected when only the second source is active;
  during step c), the first and second propagation patterns are time-reversed independently from each other in order to generate, respectively, a first reverse excitation scheme and a second reverse excitation scheme,
  at step d), the first source is controlled with the first reverse excitation scheme to generate at least a first modified shear wave and, simultaneously, the second source is controlled with the second reverse excitations scheme to generate at least a second modified shear wave, whereas the shear waves are focused at a given point of the target region.

Thanks to the invention, the modified shear waves originating from the first and second sources combine with each other and can be optimized in order to focus at a given point of the target region, independently of the actual geometry and of the linear behaviour of the soft solid. In particular, this method can be used with a damping medium which is more representative of the actual soft solids used in practical applications than a agar-gelatin phantom. High stress levels can be obtained in the target zone of the soft solid in order to obtain a non-elastic behaviour, which can be easily detected in the framework of a shear wave imaging method. Moreover, since high levels of shear waves concentration can be obtained, a substantial increase in the temperature of the target zone can also be obtained, which can be useful for a thermal mapping method or a thermal treatment method of a target region of a soft solid.

According to further aspects of the invention which are advantageous but not compulsory, the method might incorporate one or several of the following features, taken in any technically admissible configuration:

For each ultrasonic transducer of the row or for each position of the single movable ultrasonic transducer along the first direction, several points are defined, at different distances of the ultrasonic transducer along its detection direction and, during step b), for the first propagation pattern, a first displacement of the soft solid along the detection direction is detected by the ultrasonic transducer, in each point and at several time moments over a first predetermined period of time, when only the first source is active, whereas, for the second propagation pattern, a second displacement of the soft solid along the detection direction is detected by the ultrasonic transducer, in each point and at several time moments over a second predetermined period of time, when only the second source is active.

During step b) and for each of said first and second propagation patterns, a three dimensional data set is built, which includes data relating to the displacements detected, for each ultrasonic transducer of the ultrasonic transducers row or for each position of the single movable ultrasonic transducer, for each point along the detection direction of the ultrasonic transducer and for each time moment over the first or second predetermined period of time.

The number of ultrasonic transducers or the number of positions of the single movable ultrasonic transducer along the first direction is between 2 and 4096, preferably between 64 and 512, more preferably equal to about 128; the number of points defined for each ultrasonic transducer or each position is between 10 and 10000, preferably between 40 and 400, more preferably equal to about 150; and the time difference between two successive time moments of said first and second predetermined period of time is between 0.1 ms and 20 ms, preferably 0.5 ms and 2 ms, more preferably 1 ms.

The method includes an additional step e) implemented after step b) and before step d) and consisting in changing a frequency parameter of at least one detected propagation pattern.

The invention also concerns a shear wave imaging method for collecting information on a target region of a soft solid, this method comprising at least the following steps:

m) implementing a method as mentioned here-above for generating a set of combined shear waves in the target region, n) detecting the propagation pattern of the combined shear waves in the target region.

This method is more efficient than known methods since the combined shear waves generated in the target region can be more intense, to the point that they allow obtaining a non-linear behaviour of the target region. With this respect, step d) of the method for generating the at least one shear wave advantageously results in a non-linear behaviour of the target region.

Step n) is preferably implemented with the same detector unit as step b). Alternatively, step n) is implemented with an MRI or OCT (optical coherence tomography) device.

The invention also concerns a thermal mapping method for collecting information on a target region of a soft solid, this method comprising at least the following steps:

m) implementing a method as mentioned here-above for generating a set of combined shear waves in the target region, p) detecting a temperature pattern in the target region.

The invention also concerns a method for thermally treating a target region of a soft solid, this method comprising at least a step m) of implementing a method as mentioned here-above for generating a set of combined shear waves in the target region.

In the thermal mapping method and in the method for thermally treating mentioned here-above, step d) of the method for generating the at least one shear wave is advantageously implemented for a period of time of at least 10 ms.

Moreover, in the shear wave imaging method, thermal mapping method and method for thermally treating of the invention, steps a) to d) can be repeated at several locations of the ultrasonic transducer(s) along a second direction which is perpendicular to the first direction and to the detection direction of each ultrasonic transducer.

Finally, the invention relates to an installation for generating at least one shear wave in a target region of a soft solid, this installation comprising at least a first source for generating at least one first shear wave in the target region, a detector unit for detecting a first propagation pattern of the at least one first shear wave and computing means for time reversing the detected propagation pattern. This installation is characterized in that:

the installation comprises at least a second source for generating at least one second shear wave in the target region;

the detector unit is capable of detecting a second propagation pattern of the at least one second shear wave;

the detector unit includes:
  a row of ultrasonic transducers aligned on a first direction perpendicular to the detection direction of each ultrasonic transducer; or
  a single ultrasonic transducer movable along a first direction perpendicular to the detection direction;

the first and second sources and associated control means are configured to successively generate the at least one first shear wave and the at least one second shear wave in the target region;

the detector unit is configured to detect the first and second propagation patterns independently from each other, respectively when the at least one first shear wave is generated and when the at least one second shear wave is generated in the target region;

the computing means are configured to proceed to a time reversal of the first and second propagation patterns, independently from each other, and to generate a first reverse excitation scheme and a second reverse excitation scheme;

the first source is adapted to generate at least a first modified shear wave, when it is controlled on the basis of the first reverse excitation scheme, and the second source is adapted to generate, at the same time, at least a second modified shear wave, when it is controlled on the basis of the second reverse excitation scheme and the first and second sources are adapted to focus the modified shear waves at a given point of the target region.

Advantageously, the row of ultrasonic transducers and/or the single movable ultrasonic transducer is movable along a second direction perpendicular to the first direction and to the detection direction of each ultrasonic transducer, or the row of ultrasonic transducers belongs to a bi-dimensional transducer device.

BRIEF DESCRIPTION OF THE DRAWINGS

The invention will be better understood on the basis of the following description which is given in correspondence with the appended figures and as an illustrative example, without restricting the object of the invention.

In the annexed figures.

DETAILED DESCRIPTION OF SOME EMBODIMENTS

Figure 1:
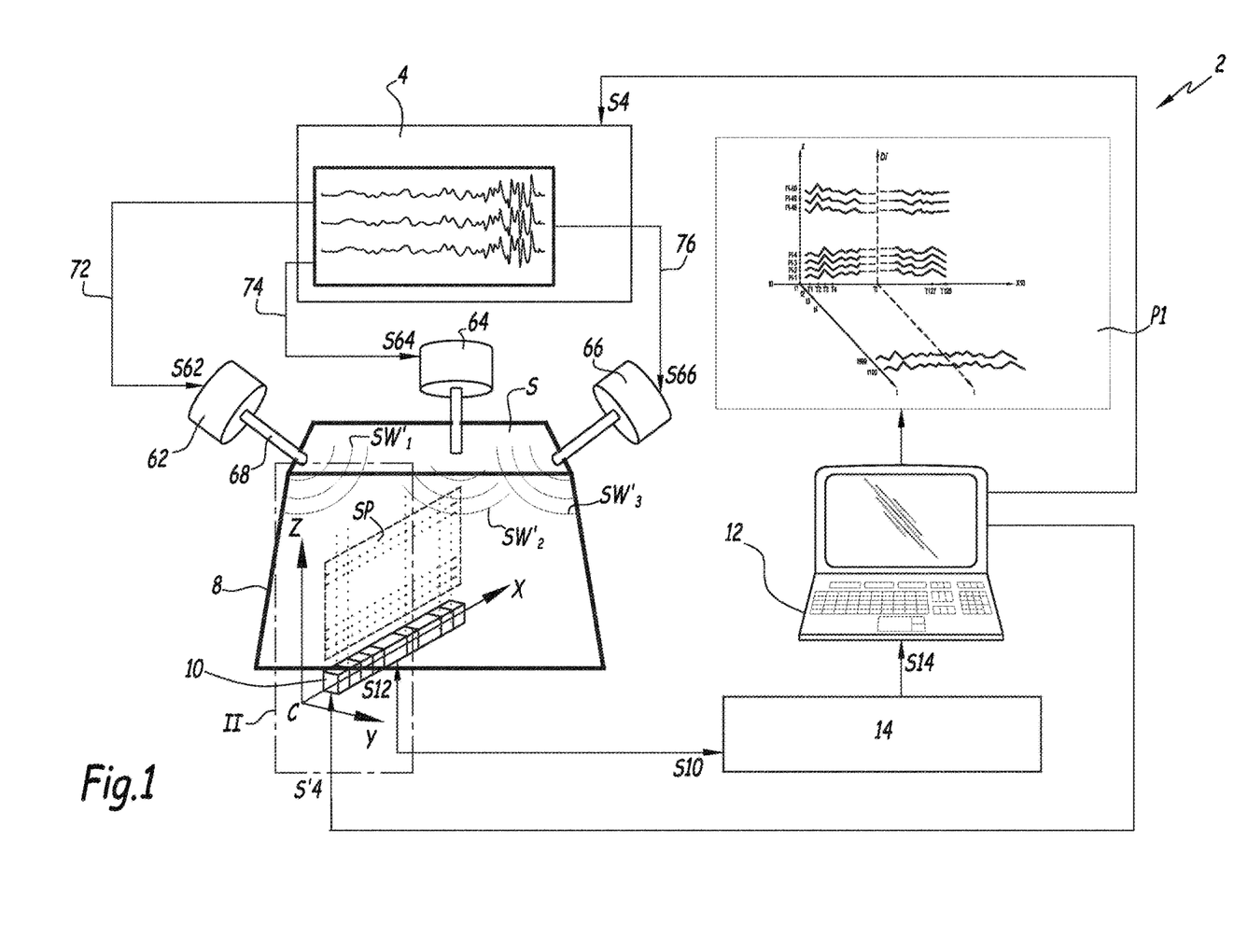
FIG. 1 is a schematic representation of an installation according to the invention.
Figure 2:
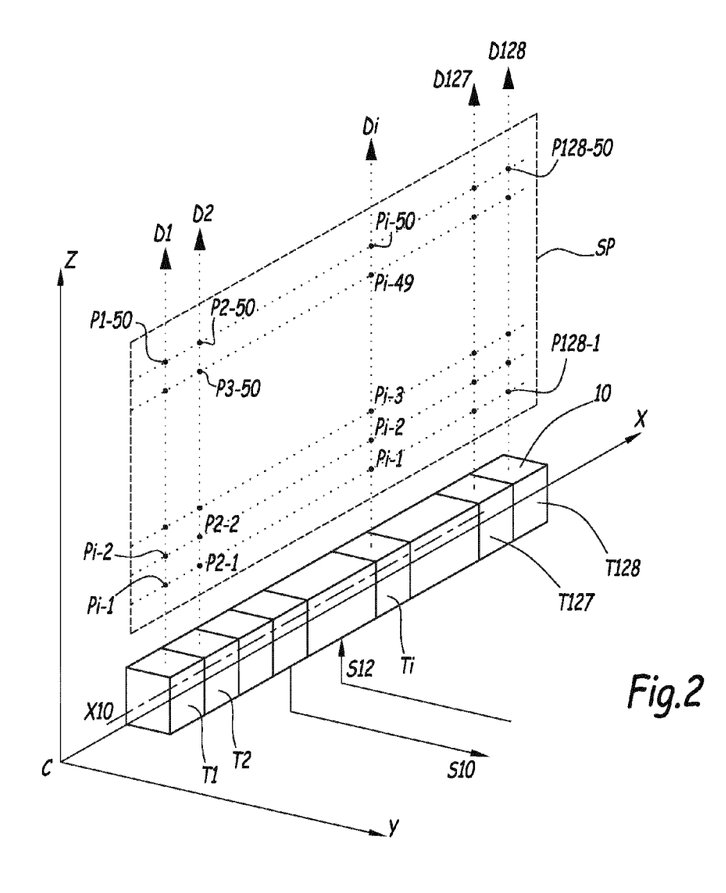
FIG. 2 is an enlarged view of detail II on FIG. 1.

The installation 2 represented on FIGS. 1 and 2 includes an alternative current generator 4 which is connected to three shear wave sources 62, 64 and 66 by respective connection lines 72, 74 and 76 through which a drive signal S62, S64 and S66 travels. Each shear wave source is made of a piston vibrator and includes a reciprocating rod 68 connected to a non represented piston included in a housing of the shear wave source.

Installation 2 also includes a box 8 where a soft solid S is housed. Box 8 is optional and can be omitted if soft solid S stands on its own. Soft solid S can be a portion of an animal body, such as a muscle or a brain, or any other soft solid mentioned here-above.

Shear wave sources 62, 64 and 68 are fixedly mounted on box 8, with their respective rods 68 in contact with one surface of soft solid S. The location of sources 62, 64 and 66 is kept for all steps of the method of the invention.

An array 10 of one hundred and twenty eight ultrasonic transducers is located below soft solid S. For each ultrasonic transducer T1 to T128, one defines its detection direction as a vertical direction D1 to D128 which goes upwardly from each ultrasonic transducer. The detection direction of each ultrasonic transducer is thus oriented towards the soft solid S, X10 denotes the longitudinal axis of array 10.

X, Y, Z denotes an orthogonal coordinate system with axis X parallel to axis X10 and axis Z parallel to directions D1 to D128. The center C of this orthogonal coordinate system is located on axis X10 in the configuration of installation 2 represented on FIGS. 1 and 2. Thus, axes X and X10 are superimposed. Array 10 is movable along axis Y, while axis X10 remains parallel to axis X.

For each ultrasonic transducer Ti, with i an integer between 1 and 128, one defines a series of one hundred and fifty points Pi-1, Pi-2, Pi-3 . . . to Pi-150 aligned along the detection direction Di of this transducer, with each point Pi-i being closer to the ultrasonic transducer Pi than point Pi-j+1, with j an integer between 1 and 149. In other words, a series of points PH is defined above each transducer Ti, with i between 1 and 128 and j between 1 and 150. In practice, points Pi-j are regularly distributed along each direction Di, between a minimum distance defined by point Pi-1 and a maximum distance defined by point Pi-150. Thus, as shown on FIG. 2, an imaginary surface SP is defined above ultrasonic transducers array 10, in a plane defined by axes X10 and Z and this imaginary surface includes a set of 6400 points Pi-j, with i between 1 and 128 and j between 1 and 150.

Each ultrasonic transducer Ti is configured to detect, in each point PH above it, a local displacement of soft solid S, in a direction parallel to axis Z.

Figure 3:
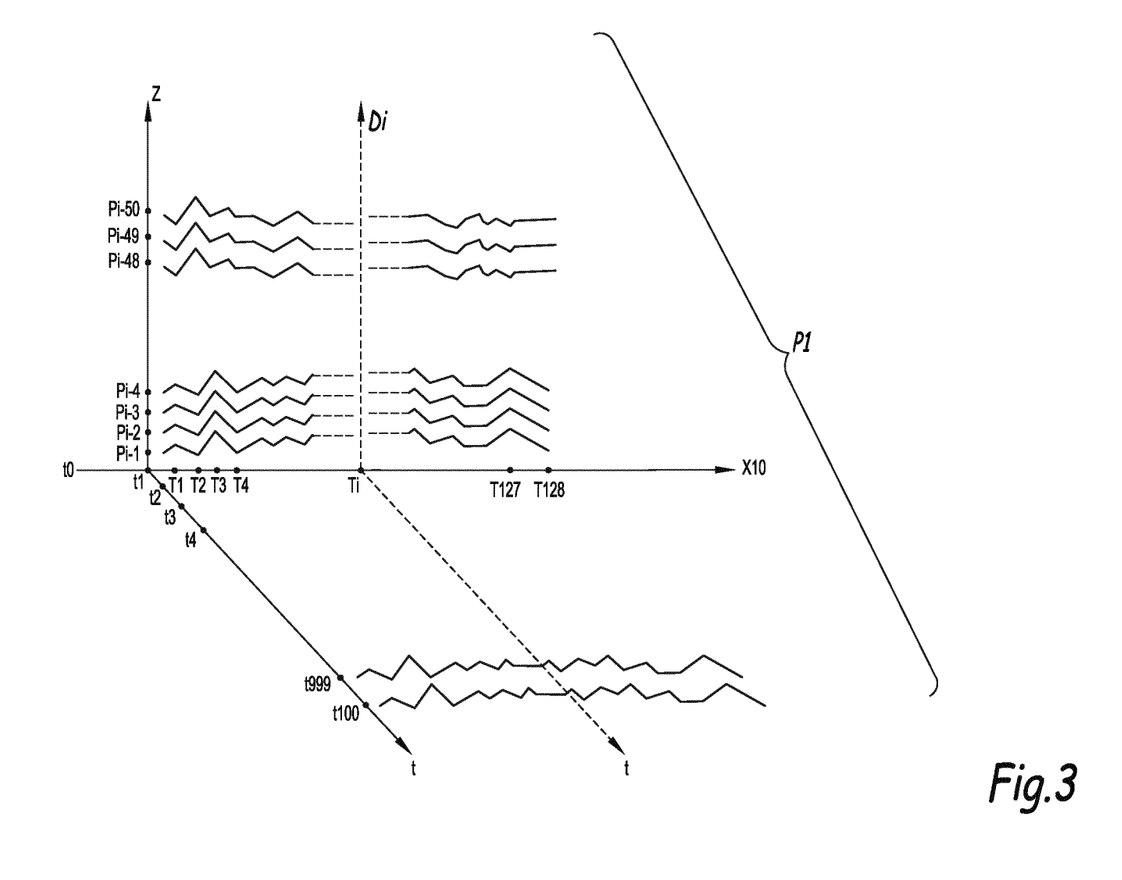
FIG. 3 is a schematic representation of a propagation pattern of a shear wave in the installation of FIGS. 1 and 2.

Thus, when one or more of the shear wave sources 62, 64 and 66 is actuated by generator 4, array 10 is capable of detecting a displacement field within imaginary surface SP, this displacement field being schematically represented on FIG. 3 at a time moment t1, above axis line X10.

Installation 2 also includes a personal computer 12 and an ultrafast ultrasound scanner 14. The output data of array 10 is forwarded to scanner 14 as a first signal S10 and, from scanner 14 to PC 12 as a second signal S14. Signals S10 and S14 transit through respective electric conductors or wirelessly.

Once it receives signal S14, computer 12 is capable of amending the data received from array 10, as explained here-under.

Figure 4:
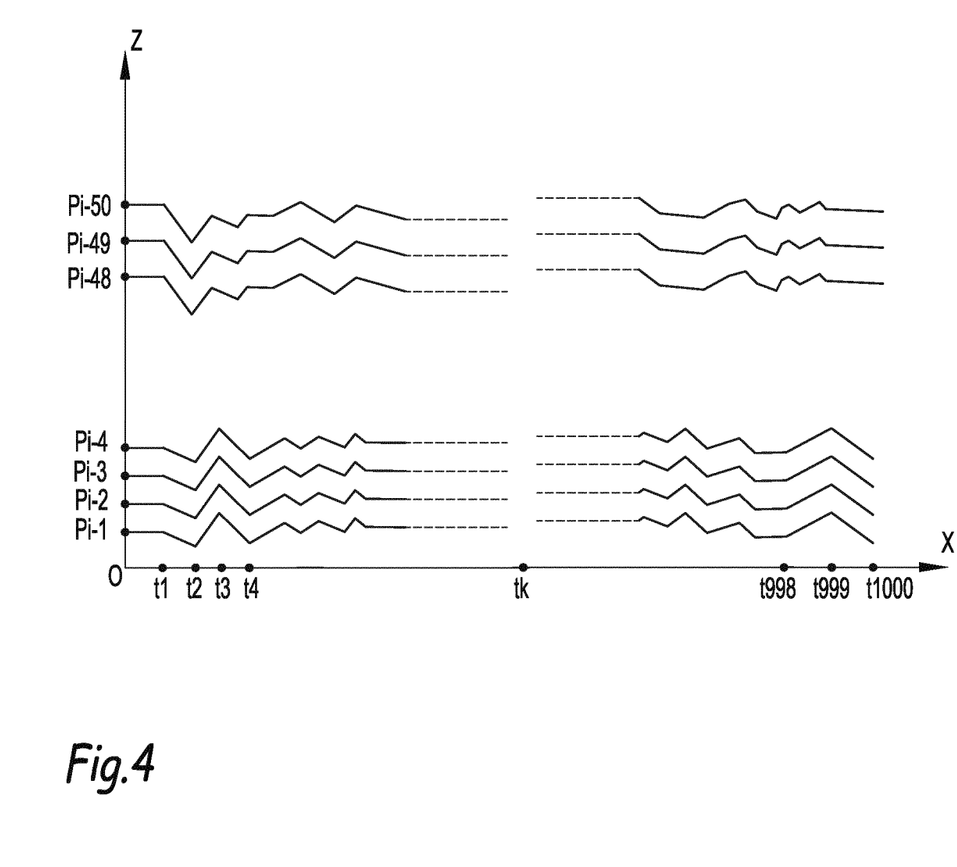
FIG. 4 is a representation, over time, of a propagation pattern for one ultrasonic detector of the installation of FIGS. 1 and 2

Consider ultrasonic transducer Ti with i between 1 and 128. Over a given period of time, say one second, ultrasonic transducer Ti detects the displacement along direction Di in each point PH every one millisecond. In other words, one thousand time moment tk, with k an integer between 1 and 1000, are to be considered for a predetermined period of one second and each transducer Ti can detect a set of vertical displacements, parallel to its detection direction Di, in each point Pi-j and at each time moment tk. This is schematically represented on FIGS. 3 and 4 where the time axis on FIG. 3 represents the possibility of variation with time t of the curves represented in the plane of axes X10 and Z. On FIG. 4, a displacement field, as sensed by ultrasonic transducer Ti, is represented over a period of time of one second. The plane of FIG. 4 is a plane parallel to axes t and Z on FIG. 3, this plane passing in the middle of transducer Ti. This plane is identified by two dotted lines on FIG. 3.

If one needs to focus the shear waves originating from the three shear wave sources 62, 64 and 66 at a given point, it is necessary to efficiently drive each source via generator 4. To this end, one implements the method of the invention represented on FIG. 5.

Figure 5:
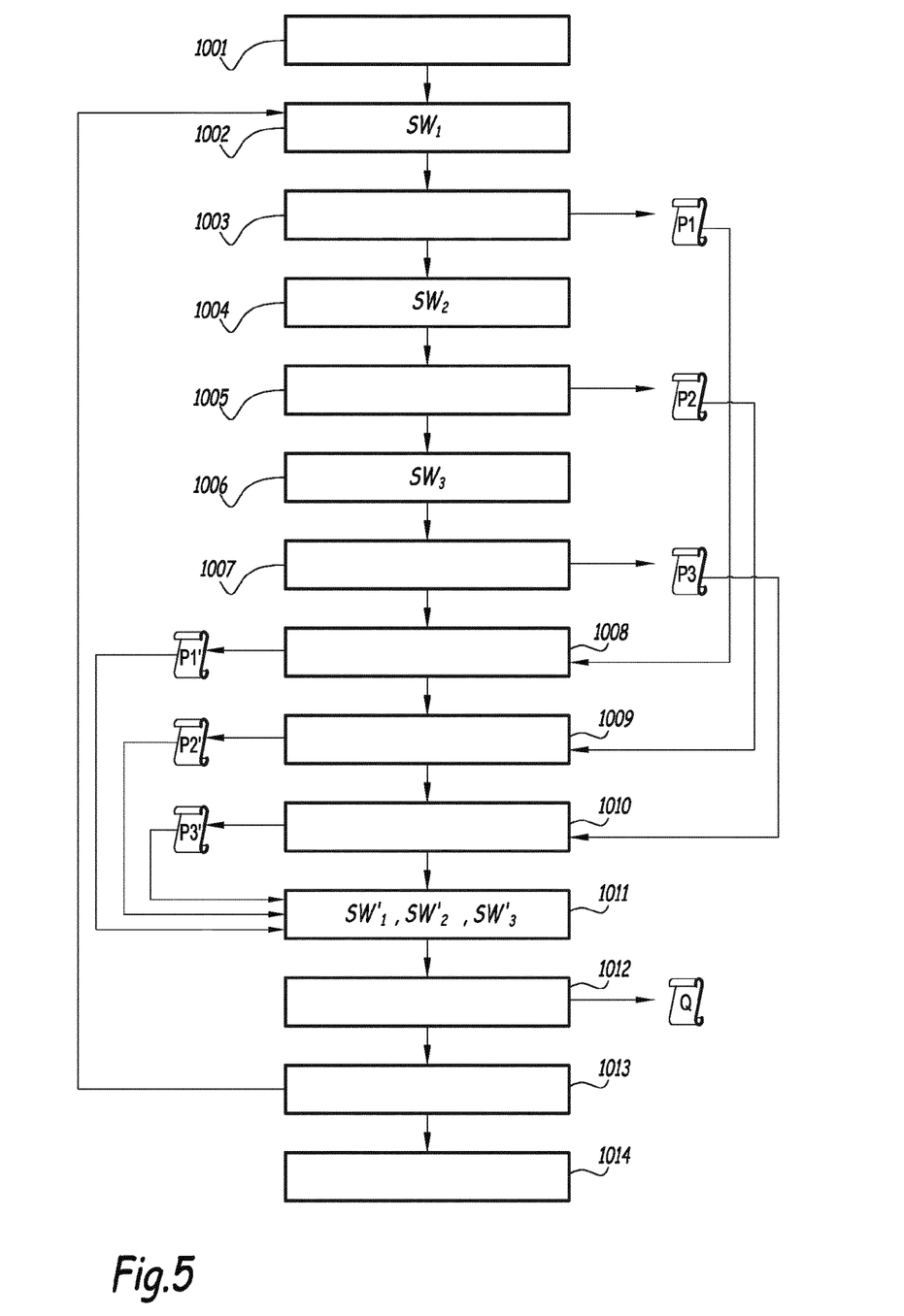
FIG. 5 is a block diagram of a method of the invention.

In a first step 1001, devices 4, 12 and 14 are started.

In a second step 1002, computer 12 drives generator 4 with an electronic signal S4 in order to actuate source 62 and not to actuate sources 64 and 66. Under such conditions, only one shear wave source 62 is active to generate one or several shear wave(s) $SW_1$ in soft solid S. When shear wave source 62 is active, ultrasonic transducer array 10 is actuated via a second signal S12 issued by computer 12 in order to detect a shear wave propagation pattern of shear wave(s) $SW_1$ originating from source 62 and propagating within soft solid S. A target region is defined by the imaginary surface SP defined above array 10 and where transducers Ti can detect shear wave(s) $SW_1$. Actuation of array 10 when only shear wave source 62 is active occurs for a predetermined time period $\Delta T1$ of one second, with a set of data acquired by transducers Ti every one millisecond (ms).

Under such circumstances, one acquires a propagation pattern which is a set of data showing the local displacement at points Pi-j, along directions D2 parallel to axis Z, and for each time moment tk between time moment t1 and t1000. In the example where i is between 1 and 128, j between 1 and 50 and k between 1 and 1000, the first propagation pattern P1, which is systematically represented on FIG. 3 and acquired during time period $\Delta T1$ includes 128×150× 1000=19 200 000 values corresponding to local vertical displacements of soft solid S.

Actually, the vertical displacement defined here-above is the Z-component of the displacement field at a point Pi-j.

$\phi_Z$ (Pi-j, tk) denotes the Z-component of the displacement field at point Pi-j and time moment tk. The data set or propagation pattern P1 represented on FIG. 3 is actually a set of values of $\phi_Z$.

$\phi_Z$ is expressed as a time convolution product between a signal $e_{62}$ (tk) emitted by source 62 at a time moment tk, oriented in any direction d and the impulse response between the d and Z-components of the source and the receiver respectively, that is hdz (Pi-j, tk). In other words, the following equation prevails $$\phi_Z(Pi\text{-}j,tk) = e_{62}(tk) \otimes hdz(Pi\text{-}j,tk) \quad \text{(Equation 1)}$$

Once propagation pattern P1 has been detected in step 1003, shear wave source 62 is switched off and shear wave source 64 is switched on by generator 4, upon instructions of computer 12 transmitted via signal S4. Then, in a subsequent step 1004, shear wave source 64 generates one or several shear wave(s) $SW_2$ in soft solid S. Array 10 is actuated to detect, in a step 1005 which takes place during a second predetermined time period $\Delta T2$ of one second, a second propagation pattern P2.

Then, upon instructions of computer 12, generator 4 switches off shear wave source 64 and switches on shear wave source 66 in order to implement two further steps 1006 and 1007 respectively similar to steps 1004 and 1005 and where a third propagation pattern P3 is detected during a third predetermined time period $\Delta T3$ which lasts also one second and where one or several shear waves $SW_3$ are generated and detected.

Consider that one needs to focus the shear waves respectively originating from sources 62, 64 and 66 at one point PH of imaginary surface SP. Under such circumstances, first propagation pattern P1 is temporally inverted in a further step 1008, at the level of point Pi-j. This inversion is a time reversal of propagation pattern P1 at point Pi-j. More precisely, the inverted source signal $e_{62}^{TR}$ corresponding to source 62 for point Pi-j and time moment tk is set equal to $$e_{62}^{TR}(Pi-j, tk) = \phi_Z(Pi-j, T1-tk) \quad \text{(Equation 2)}$$
$$= e_{62}(Pi-j, T1-tk) \otimes hdz(Pi-j, T1-tk)$$

where T1 is the duration of the first predetermined period $\Delta T1$, one second in the example.

Under such circumstances, the shear wave displacement at point Pi-j and instant tk is maximized at the following value:

$$\phi^{TR}_z(Pi\text{-}j,tk) = \phi_Z(Pi\text{-}j,T1\text{-}tk) \otimes hdz(Pi\text{-}j,tk) \quad \text{(Equation 3)}$$

P1' denotes the result of the time reversal for all points Pi-j and all time moments tk. This data set is a reverse excitation scheme for points PH in imaginary surface SP.

In a further step 1009, propagation pattern P2 is temporarily inverted, according to an approach similar to the one of step 1008, in order to generate a second reverse excitation scheme P2'.

In a still further step 1010, propagation pattern P3 is also temporarily inverted, according to an approach similar to the one of step 1008, in order to generate a third reverse excitation scheme P3'.

The orders of steps 1008, 1009 and 1010 can be changed. These steps can also occur in parallel, provided that propagation patterns P1, P2 and P3 are time-reverse independently from each other.

On FIG. 1, only propagation pattern P1 is represented above computer 12, for the sake of simplicity. Actually, as mentioned here-above, computer 12 is configured to generate and compute propagation patterns P1 to P3 and reverse excitation schemes P1' to P3'.

Thereafter, shear wave sources 62, 64 and 66 are simultaneously actuated by generator 4, in a step 1011, on the basis of reverse excitation schemes P1', P2' and P3'. With this approach, modified share waves $SW'_1$, $SW'_2$ and $SW'_3$ respectively originating from sources 62, 64 and 66 at step 1011 combine or focus in each point Pi-j of imaginary surface SP as shown on FIG. 1 which represents installation 2 at step 1011. Under these conditions, if one needs to concentrate the shear waves at a point Pi-j, one uses the three reverse excitation schemes for this point, since sources 62, 64 and 66 are adapted to focus shear waves $SW'_1$, $SW'_2$ and $SW'_3$ at such a given point.

Thus, the method of steps 1001 to 1011 allows to generate modified shear waves $SW'_1$, $SW'_2$ and $SW'_3$ focused at any chosen point Pi-j, with a high energy level, which allows obtaining a non-linear behaviour of soft solid S at this point.

In step 1011, a point Pi-j of imaginary surface SP is submitted to an inverted excitation set of forces induced by the modified shear waves $SW'_1$, $SW'_2$ and $SW'_3$ originating from sources 62, 64 and 66. This excitation set of forces is based on the temporarily inverted propagation patterns P1', P2' and P3' and conveyed by the modified shear waves $SW'_1$, $SW'_2$ and $SW'_3$.

This can be used in the framework of a shear wave imaging method, where a step 1012 is implemented simultaneously with step 1011 and where a propagation pattern Q of the shear waves within soft solid S is detected with ultrasonic transducers array 10, according to an approach similar to the one of steps 1003, 1005 and 1007. In other words, the same array 10 is used for learning steps 1003, 1005 and 1007 and for the actual shear wave imaging detection step 1012.

Alternatively, a MRI or OCT device can be used in step 1012.

According to another approach, steps 1001 to 1011 can be used in the framework of a thermal mapping method in order to generate, at a given point Pi-j, some shear waves $SW'_1$, $SW'_2$ and $SW'_3$ which result in a temperature increase at this point. Then, any appropriate detecting device, such as an ultrasonic device, a MRI device or an OCT device, can be used to detect the temperature pattern of the target region, for instance a region corresponding to imaginary surface SP.

According to another approach, the method of steps 1001 to 1011 can be used in order to thermally treat a target region of a soft solid, that is to increase locally the temperature of the soft solid, in order to obtain a desired effect. Such can be the case for heating a part of a soft solid, e.g. a piece of cheese or a non metallic part of prosthesis. This can also be used to cure a living organ.

In the thermal mapping method and in the method for thermally treating, step 1011 is implemented for a period of time of at least 10 ms seconds, preferably at least 10 s seconds in order to obtain a significative temperature increase.

According to a non represented alternative embodiment of the invention, one can use, instead of array 10, a single transducer which is movable along axis X.

The method of steps 1001 to 1012 is explained here-above in case array 10 is used for a target region defined by imaginary surface SP. Actually, this method, and the corresponding shear wave imaging method, thermal mapping method and method for thermally treating a target region can be used for a target region defined by the pre-determined volume within soft solid S. In that case, array 10 is movable along axis Y, its longitudinal axis X10 remaining parallel to axis X. This allows to implement steps 1002 to 1012 at different locations of array 10 along axis Y. In such a case, a method according to the invention includes a further step 1013 where array 10 is moved of a predetermined step along axis Y. Then, the method is started again at step 1002. Once all positions necessary to cover the predetermined volume have been reached along axis Y, the method stops at step 1014.

According to still another embodiment of the invention, instead of using a single array 10, several such arrays can be installed next to each other along axis Y. These arrays can be used one after the other, which is implemented in a step equivalent to step 1013 where, instead of moving array 10, one switches from one array to the other.

Alternatively, a bi-dimensional transducer device can be used which includes rows and columns of ultrasonic transducers respectively aligned along directions parallel to axis X and Y.

The invention does not depend on the precise location of shear wave sources 62, 64 and 66 with respect to box 8 and soft solid S. Actually, since the propagation patterns P1 to P3 are collected once these sources are fixedly installed with respect to soft solid S, the time reversal of these patterns are performed on the basis of data collected with the actual positions of these sources, so that these positions are taken into account to generate reverse excitation schemes P1', P2' and P3'. In other words, the method of the invention is self adapting with respect to the actual positions of the shear wave sources with respect to the soft solid.

The method is described here-above in case one uses three shear wave sources. It works with two shear wave sources or with a number of shear wave sources larger or equal to 4. In practice, the number of shear wave sources is advantageously chosen between 8 and 64, preferably between 10 and 15.

The actual number of ultrasonic transducers Ti of array 10 can be between 2 and 4096, preferably between 64 and 512, the value of 128 being preferred since it corresponds to products available on the market, e.g. from company Philips with reference ATL L7-4 linear array.

The number of points Pi-j defined on the detection direction Di of an ultrasonic transducer Ti is between 10 and 10000, preferably between 40 and 400. The value of 150 is, in practice, very convenient.

The time interval between two successive time moments tk can be different from 1 ms. It is chosen between 0.1 ms and 10 ms, preferably between 0.5 ms and 2 ms, depending on the actual durations T1, T2, etc. of the time period used.

According to an optional aspect of the invention, which is not represented on FIG. 5, the method includes an additional step, between step 1003 and step 1012, where a frequency parameter of propagation pattern P1 is changed. Similar steps can exist for propagation patterns P2 and P3. This allows eliminating or enhancing some harmonics of the propagation patterns. Manipulating the frequency content of shear waves might enhance the efficiency of the focusing.

One potential use of the invention concerns the generation of shear waves in the brain of a human being or an animal for brain function modulation. In particular, focusing shear waves into primary and/or secondary somato-sensory areas of the brain may help controlling the level of pain felt by a patient or facilitate recovery after a cerebral vascular accident.

The embodiments and alternative embodiments considered here-above can be combined to generate new embodiments of the invention.

The invention claimed is:

1. A method for generating at least one shear wave in a target region of a soft solid, the method including at least the following steps:
    a) generating the at least one shear wave in the target region;
    b) detecting a propagation pattern of the at least one shear wave in the target region;
    c) proceeding to a time reversal of the detected propagation pattern; and
    d) submitting the target region to an excitation set of forces based on the temporally inverted propagation pattern,
    wherein:
        step a) is implemented by generating at least two shear waves with at least a first source of shear waves and at least a second source of shear waves,
        step b) is implemented with a detector unit which includes:
            a row of ultrasonic transducers aligned in a first direction perpendicular to a detection direction of each ultrasonic transducer, or
            a single ultrasonic transducer movable along a first direction perpendicular to a detection direction,
        during step b), a first propagation pattern is detected when only the first source is active and a second propagation pattern is detected when only the second source is active,
        during step c), the first and second propagation patterns are time-reversed independently from each other in order to generate, respectively, a first reverse excitation scheme and a second reverse excitation scheme, and
        at step d), the first source is controlled with the first reverse excitation scheme to generate at least a first modified shear wave, and, simultaneously, the second source is controlled with the second reverse excitation scheme to generate at least a second modified shear wave, the at least first modified shear wave and the at least second modified shear wave being focused at a given point of the target region.

2. The method according to claim 1, wherein, for each ultrasonic transducer of the row or for each position of the single movable ultrasonic transducer along the first direction, several points are defined, at different distances of the ultrasonic transducer along its detection direction, and
    during step b),
        for the first propagation pattern, a first displacement of the soft solid along the detection direction is detected by the ultrasonic transducer, in each point and at several time moments over a first predetermined period of time, when only the first source is active, and for the second propagation pattern, a second displacement of the soft solid along the detection direction is detected by the ultrasonic transducer, in each point and at several time moments over a second predetermined period of time, when only the second source is active.

3. The method according to claim 2, wherein, during step b) and for each of said first and second propagation patterns, a three-dimensional data set is built, which includes data relating to the displacements detected for each ultrasonic transducer of the ultrasonic transducers row or for each position of the single movable ultrasonic transducer, for each point along the detection direction of the ultrasonic transducer, and for each time moment over the first or second predetermined period of time.

4. The method according to claim 2, wherein the number of ultrasonic transducers or the number of positions of the single movable ultrasonic transducer along the first direction is between 2 and 4096, the number of points defined for each ultrasonic transducer or each position is between 10 and 10000, and the time difference between two successive time moments of said first and second predetermined period of time is between 0.1 ms and 10 ms.

5. The method according to claim 1, further comprising an additional step implemented after step b) and before step d) and consisting of:

e) changing a frequency parameter of at least one detected propagation pattern.

6. A shear wave imaging method for collecting information on a target region of a soft solid, the method comprising at least the following steps:

implementing a method for generating a set of combined shear waves in the target region, the method for generating the set of combined shear waves including at least the following steps:

a) generating at least one shear wave in the target region, b) detecting a propagation pattern of the at least one shear wave in the target region, c) proceeding to a time reversal of the detected propagation pattern, and d) submitting the target region to an excitation set of forces based on the temporally inverted propagation pattern, wherein:

step a) is implemented by generating at least two shear waves with at least a first source of shear waves and at least a second source of shear waves, step b) is implemented with a detector unit which includes:

a row of ultrasonic transducers aligned in a first direction perpendicular to a detection direction of each ultrasonic transducer, or a single ultrasonic transducer movable along a first direction perpendicular to a detection direction, during step b), a first propagation pattern is detected when only the first source is active and a second propagation pattern is detected when only the second source is active, during step c), the first and second propagation patterns are time-reversed independently from each other in order to generate, respectively, a first reverse excitation scheme and a second reverse excitation scheme, and at step d), the first source is controlled with the first reverse excitation scheme to generate at least a first modified shear wave, and, simultaneously, the second source is controlled with the second reverse excitation scheme to generate at least a second modified shear wave, the at least first modified shear wave and the at least second modified shear wave being focused at a given point of the target region; and detecting a propagation pattern of the set of combined shear waves in the target region.

7. The method according to claim 6, wherein step d) of the method for generating the at least one shear wave results in a non-linear behavior of the target region.

8. The method according to claim 6, wherein the detecting the propagation pattern is implemented with the same detector unit as step b).

9. The method according to claim 6, wherein the detecting the propagation pattern is implemented with an MRI or OCT device.

10. The method according to claim 6, wherein steps a) to d) are repeated at several locations of the ultrasonic transducers along a second direction perpendicular to the first direction and to the detection direction of each ultrasonic transducer.

11. A thermal mapping method for collecting information on a target region of a soft solid, the method comprising at least the following steps:

implementing a method for generating a set of combined shear waves in the target region, the method for generating the set of combined shear waves including at least the following steps:

a) generating at least one shear wave in the target region, b) detecting a propagation pattern of the at least one shear wave in the target region, c) proceeding to a time reversal of the detected propagation pattern, and d) submitting the target region to an excitation set of forces based on the temporally inverted propagation pattern, wherein:

step a) is implemented by generating at least two shear waves with at least a first source of shear waves and at least a second source of shear waves, step b) is implemented with a detector unit which includes:

a row of ultrasonic transducers aligned in a first direction perpendicular to a detection direction of each ultrasonic transducer, or a single ultrasonic transducer movable along a first direction perpendicular to a detection direction, during step b), a first propagation pattern is detected when only the first source is active and a second propagation pattern is detected when only the second source is active, during step c), the first and second propagation patterns are time-reversed independently from each other in order to generate, respectively, a first reverse excitation scheme and a second reverse excitation scheme, and at step d), the first source is controlled with the first reverse excitation scheme to generate at least a first modified shear wave, and, simultaneously, the second source is controlled with the second reverse excitation scheme to generate at least a second modified shear wave, the at least first modified shear wave and the at least second modified shear wave being focused at a given point of the target region; and
detecting a temperature pattern of the target region.

12. The method according to claim 11, wherein step d) of the method for generating the at least one shear wave is implemented for a period of time of at least 10 ms seconds.

13. The method according to claim 11, wherein steps a) to d) are repeated at several locations of the ultrasonic transducers along a second direction perpendicular to the first direction and to the detection direction of each ultrasonic transducer.

14. A method for thermally treating a target region of a soft solid, the method comprising at least the following step:
implementing a method for generating a set of combined shear waves in the target region, the method for generating the set of combined shear waves including at least the following steps:
a) generating at least one shear wave in the target region,
b) detecting a propagation pattern of the at least one shear wave in the target region,
c) proceeding to a time reversal of the detected propagation pattern, and
d) submitting the target region to an excitation set of forces based on the temporally inverted propagation pattern,
wherein:
step a) is implemented by generating at least two shear waves with at least a first source of shear waves and at least a second source of shear waves,
step b) is implemented with a detector unit which includes:
a row of ultrasonic transducers aligned in a first direction perpendicular to a detection direction of each ultrasonic transducer, or
a single ultrasonic transducer movable along a first direction perpendicular to a detection direction,
during step b), a first propagation pattern is detected when only the first source is active and a second propagation pattern is detected when only the second source is active,
during step c), the first and second propagation patterns are time-reversed independently from each other in order to generate, respectively, a first reverse excitation scheme and a second reverse excitation scheme, and
at step d), the first source is controlled with the first reverse excitation scheme to generate at least a first modified shear wave, and, simultaneously, the second source is controlled with the second reverse excitation scheme to generate at least a second modified shear wave, the at least first modified shear wave and the at least second modified shear wave being focused at a given point of the target region.

15. The method according to claim 14 wherein step d) of the method for generating the at least one shear wave is implemented for a period of time of at least 10 ms seconds.

16. The method according to claim 14 wherein steps a) to d) are repeated at several locations of the ultrasonic transducers along a second direction perpendicular to the first direction and to the detection direction of each ultrasonic transducer.

17. A system for generating at least one shear wave in a target region of a soft solid, the system comprising:
at least a first source configured to generate at least one first shear wave in the target region;
a detector unit configured to detect a first propagation pattern of the at least one first shear wave;
a computing system for time reversing the detected propagation pattern; and
at least a second source configured to generate at least one second shear wave in the target region,
wherein
the detector unit is configured to detect a second propagation pattern of the at least one second shear wave,
the detector unit includes:
a row of ultrasonic transducers aligned on a first direction perpendicular to a detection direction of each ultrasonic transducer; or
a single ultrasonic transducer movable along a first direction perpendicular to a detection direction;
the first and second sources and associated controllers are configured to successively generate the at least one first shear wave and the at least one second shear wave in the target region,
the detector unit is configured to detect the first and second propagation patterns independently from each other, respectively when the at least one first shear wave is generated and when the at least one second shear wave is generated in the target region;
the computing system is configured to proceed to a time reversal of the first and second propagation patterns, independently from each other, and to generate a first reverse excitation scheme and a second reverse excitation scheme;
the first source is configured to generate at least a first modified shear wave, when the first source is controlled on the basis of the first reverse excitation scheme, and the second source is configured to generate, at the same time, at least a second modified shear wave, when the second source is controlled on the basis of the second reverse excitation scheme and the first and second sources are configured to focus the modified shear waves at a given point of the target region.

18. The system according to claim 17, wherein the row of the ultrasonic transducers or the single movable ultrasonic transducer is movable along a second direction perpendicular to the first direction and to the detection direction of each ultrasonic transducer or the row of ultrasonic transducers belongs to a bi-dimensional transducer device.

19. The method according to claim 4, wherein the number of ultrasonic transducers or the number of positions of the single movable ultrasonic transducer along the first direction is between 64 and 512.

20. The method according to claim 4, wherein the number of points defined for each ultrasonic transducer or each position is between 40 and 400.

21. The method according to claim 4, wherein the time difference between two successive time moments of said first and second predetermined period of time is between 0.5 ms and 2 ms.

* * * * *